United States Patent [19]

Chalek et al.

[11] Patent Number: 5,853,367

[45] Date of Patent: Dec. 29, 1998

[54] TASK-INTERFACE AND COMMUNICATIONS SYSTEM AND METHOD FOR ULTRASOUND IMAGER CONTROL

[75] Inventors: Carl Lawrence Chalek, Scotia; William Macomber Leue, Albany; William Thomas Hatfield, Schenectady, all of N.Y.

[73] Assignee: General Electric Company, Schenectady, N.Y.

[21] Appl. No.: 819,237

[22] Filed: Mar. 17, 1997

[51] Int. Cl.[6] .................................................. A61B 8/00
[52] U.S. Cl. ............................... 600/437; 128/916
[58] Field of Search .................... 600/437, 443, 600/438, 458; 128/916; 364/474.24

[56] References Cited

U.S. PATENT DOCUMENTS 5,709,206  1/1998  Teboul ..................................... 600/437
5,778,177  7/1998  Azar ......................................... 128/916

*Primary Examiner*—Marvin M. Lateef
*Assistant Examiner*—Maulin Patel
*Attorney, Agent, or Firm*—Marvin Snyder; Douglas E. Stoner

[57] ABSTRACT

Complex equipment operated by a plurality of computerized task functions is coupled to a host processor which controls operation of a plurality of task functions performed by the equipment. Included in the equipment are a plurality of client processors, a communications network coupling the host processor to the client processors, and a plurality of programs providing respective task interfaces for running selected task functions of the equipment on any of the client processors as remote processes. Each task interface program includes a library of communications handlers and a designated task interface. When the complex equipment comprises an ultrasound imager system, the task functions of shaping a transmit waveform and shading the transducer reception parameters are performed through preferred embodiments of such task interfaces. A voice input task function may also be run as a remote process coupled to the imager host through the network interface.

20 Claims, 9 Drawing Sheets

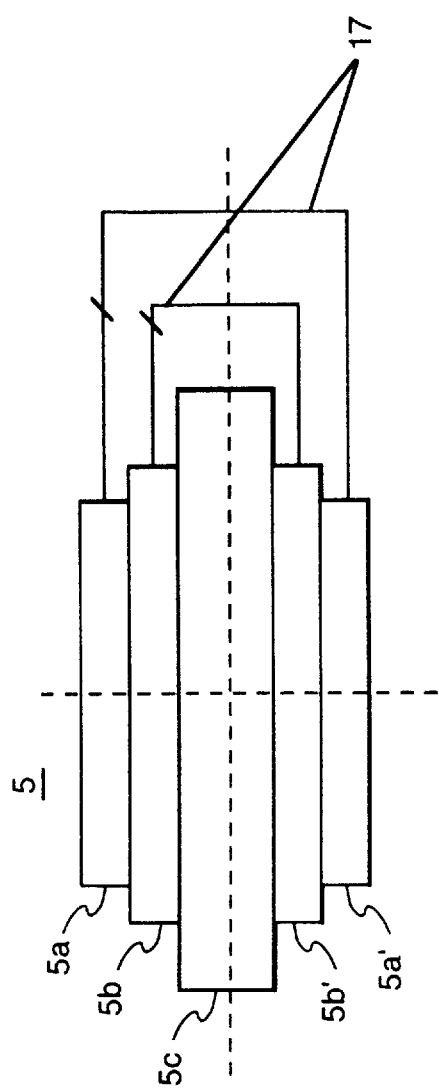
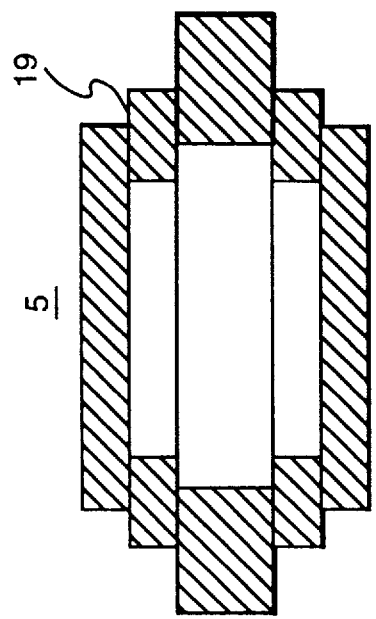
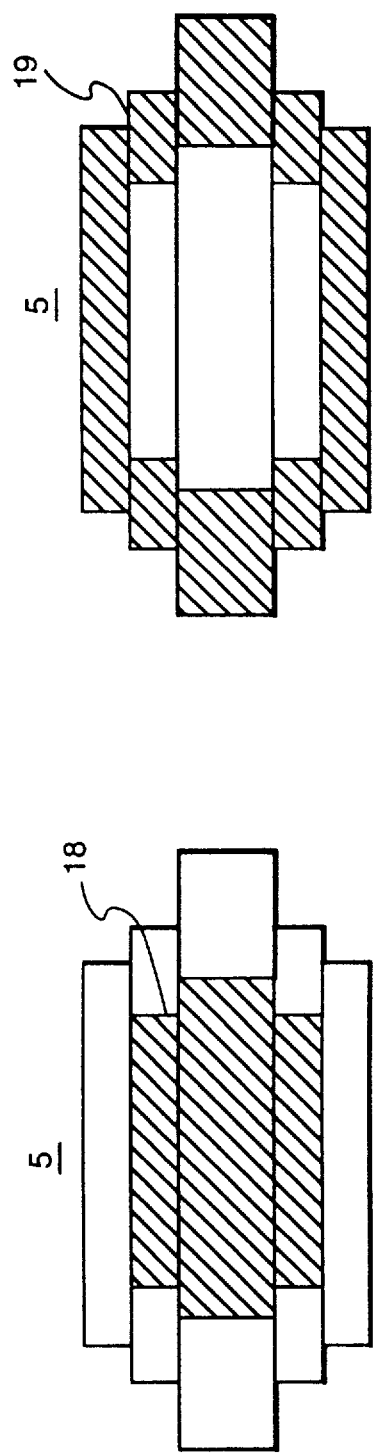
FIG. 3a
FIG. 3b
FIG. 3c

TASK-INTERFACE AND COMMUNICATIONS SYSTEM AND METHOD FOR ULTRASOUND IMAGER CONTROL

FIELD OF THE INVENTION

This invention relates to a system and method for controlling an ultrasound imager or other complex equipment employing computer processor control of task functions. In particular, the invention relates to a communications system and method which optimizes the distribution of task loadings for complex computerized equipment.

BACKGROUND OF THE INVENTION

Complex equipment increasingly relies upon the speed, memory, and computational power of computer processors under software program control to operate diverse functions digitally. For example, conventional ultrasound imager systems employ microprocessors to provide digital control of hardware to generate an ultrasound waveform from an array of piezoelectric elements of a probe transducer during a transmission cycle, and to convert analog echoes received by the transducer to digital image data during a reception cycle.

Recent advances have employed digital techniques to control generation of an ultrasound wave so that it is optimally shaped for different scan types (point scan, line scan, plane scan, depth scan, etc.) and directionally phased for scanning over an area of the subject without having to reposition the probe. For a detailed description of such digital ultrasound transmitter techniques, reference is made to commonly assigned U.S. Pat. Nos. 5,014,712 issued May 14, 1991 and entitled "Coded Excitation For Transmission Dynamic Focusing of Vibratory Energy Beam", and 5,345,939 issued Sep. 13, 1994 and entitled "Ultrasound Imaging System With Dynamic Window Function", both being incorporated herein by reference.

Digital techniques have also been employed to selectively attentuate or filter the received echo signals for an ultrasound imager with a dynamic "windowing" function so that spurious echo signals are eliminated and a highly resolved scan image is obtained. For detailed description of such digital ultrasound reception techniques, reference is made to commonly assigned U.S. Pat. Nos. 4,839,652 issued Jun. 13, 1989 and entitled "Method and Apparatus For High Speed Digital Phased Array Coherent Imaging System", 4,896,287 issued Jan. 23, 1990 and entitled "Cordic Complex Multiplier", 4,983,970 issued Jan. 8, 1991 and entitled "Method and Apparatus For Digital Phased Array Imaging", 5,230,340 issued Jul. 27, 1993 and entitled "Ultrasound Imaging System With Improved Dynamic Focusing", and 5,345,939 issued Sep. 13, 1994 and entitled "Ultrasound Imaging System With Dynamic Window Function", all being incorporated herein by reference.

The employment of increasingly complex and computationally intensive ultrasound transmitter and reception techniques has imposed greater task loading on the processor system controlling the imager. User controls for the ultrasound imager include a plurality of arrays of switches, sliding and rotary potentiometers, input devices, and dedicated display(s) used to control and track the multiple task functions to be performed by or with the imager. For example, dedicated I/O devices and controls may be needed for the task functions of calibrating the imager, setting the scan type and sequencing, setting the transmitted waveform shape, setting the image reception parameters, controlling channel parameters for the transducer elements, etc. In addition, there is usually a facility for operator 110 consisting of a display screen (separate from the main system display) and associated menu system implemented as a touch screen or software configured switches.

The conventional equipment interface is not easily reconfigured, so that adding or customizing new features may be difficult or impossible without substantial re-engineering and hardware modifications. Even built-in software-configurable menu systems are often constrained in their capabilities by available semiconductor chip space, processor capacity and other limitations.

It is therefore desirable to provide a way of controlling complex equipment employing computer processor control of task functions, and in particular for optimizing distribution of task loadings for such complex computerized equipment.

SUMMARY OF THE INVENTION

In accordance with an embodiment of the invention, a system for controlling complex equipment operated by a plurality of computerized task functions includes a host processor coupled to the complex equipment for controlling operation of the plurality of task functions, a plurality of client processors, a communications network coupling the host processor to the client processors, and a plurality of programs for providing respective task interfaces for running selected task functions of the complex equipment on any of the client processors as remote processes. In this manner resource-intensive task loadings for the complex equipment can be distributed to remote processors as separately run processes. This allows a high degree of flexibility and customization in running the task functions and reduces the burden on the host processor.

Each task interface program includes of a library of communications handlers and a designated task interface. The communications library contains functions to request connection to the host, send commands to the host, receive acknowledgements and information from the host, and close the connection with the host. Server software on the host processor contains functions to listen for connection requests from clients, establish connections in prioritized order, respond to commands and send information to clients, and close connections with clients. A common task interface builder may be used to construct the task interface programs. The task interface builder allows graphical interface controls to be configured specifically for each task function and eliminates the need for fixed hardware I/O devices and manual controls wherever appropriate.

As an example of complex equipment, the resource-intensive task functions of an ultrasound imager system, such as calibrating the imager, setting the scan type and sequencing, shaping a transmitted waveform, shading the transducer reception parameters, etc., can be off-loaded from the host processor to other computers running them as remote processes.

The invention also includes, for an ultrasound imager system, specific improvements in a task interface for waveform shaping, a task interface for echo reception shading, and a voice input interface for spoken commands to the host processor.

BRIEF DESCRIPTION OF THE DRAWINGS

FIG. 3a is a schematic diagram of a multi-row transducer probe for an ultrasound imager, and FIGS. 3b and 3c illustrate a two-step firing mode for the probe.

DETAILED DESCRIPTION OF THE PREFERRED EMBODIMENTS

A preferred embodiment of the task-interface and communications system and method in accordance with the present invention is described below with respect to the example of an ultrasound imager system. However, the disclosed principles of the invention are equally applicable to other types of complex equipment employing computerized control of task functions.

Communications System and Method

Figure 1:
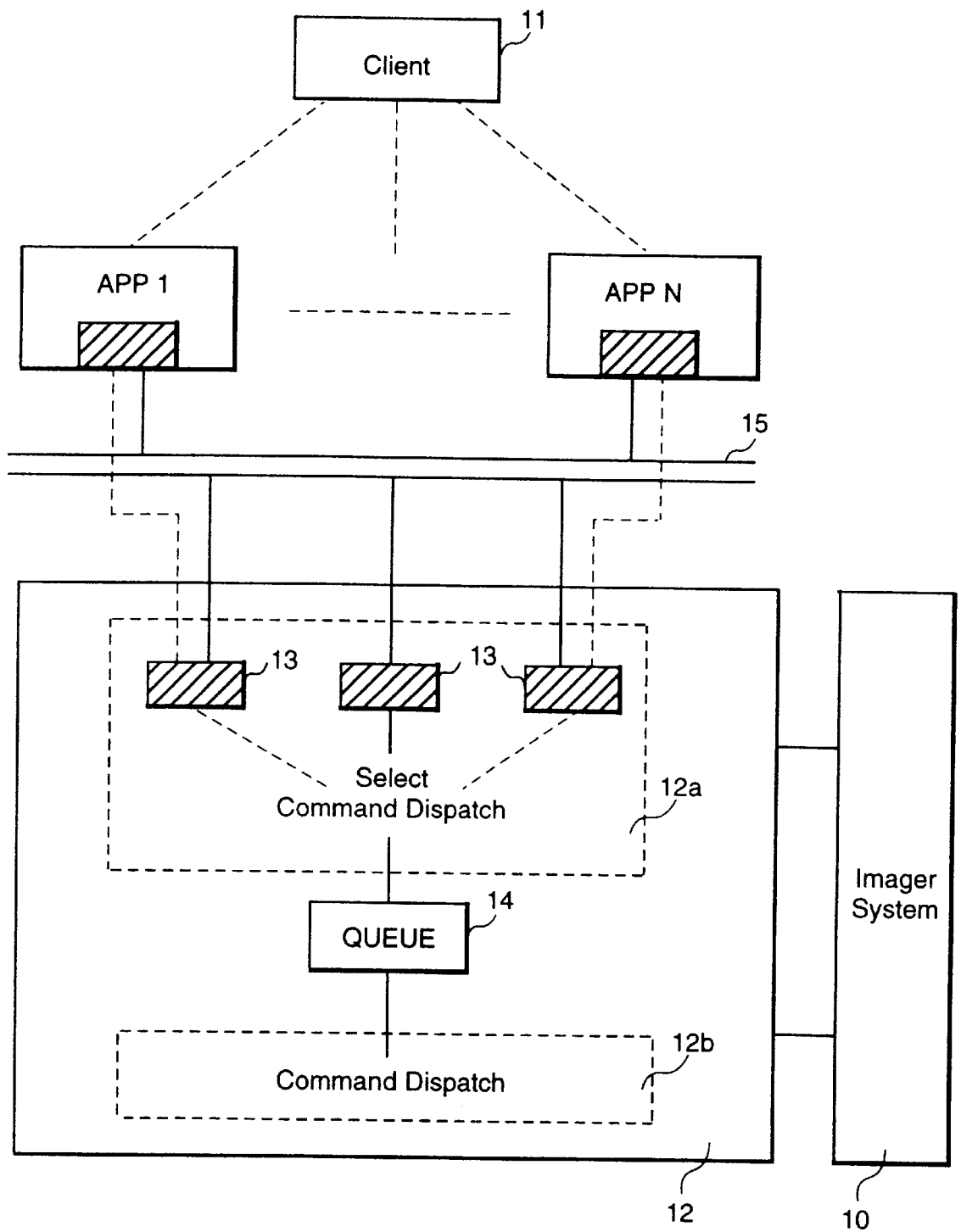
FIG. 1 schematically illustrates a communications system and method for controlling complex equipment, such as an ultrasound imager system, in accordance with the present invention.

FIG. 1 depicts the overall architecture of the preferred communications system and method for computerized control of an ultrasound imager system 10. System 10 is operated under control of a host processor 12 connected in a client-server arrangement via a communications network 15 with a plurality of client processors 11 running remote processes which are designated APP-1, . . . , APP-N. The client processors are other computers remote from the host processor, such as workstations or PCs. Ultrasound imager system 10 is conventional and not described in further detail herein. Reference is made to the commonly assigned patents identified above for more detailed explanation of the components and functions of conventional ultrasound imager systems.

Communications network 15 has a plurality of communications channels which may be, for example, Internet sockets or serial (RS-232) or other types of local area network (LAN) connections. For Internet socket connections, both the client and server operating systems support establishment of a communications link via socket pairs. At the server, available sockets 13 are assigned by server software to link with remote processes requesting connection. The number of sockets available depends on the resources made available on the host. The communication handlers of the client and the host rely on lower-level system calls to establish connections.

Host processor 12, in its role as the server in this client-server configuration, handles two basic tasks at its operating system level. A communications task 12a is devoted to socket management and command dispatch when it listens on the available Internet sockets for clients requesting connection. It accepts connections until there are no more sockets available. Once connections are established, the communications task waits for command requests from the connected clients and either handles the requests directly (by calling handler functions) or passes them on to a queue 14 for processing by a background task 12b at a lower priority.

The separation of communications and background tasks is used to provide better response to clients. The host can respond with acknowledgements, downloaded programs, data, or other information to a client, and closes the connection when the task is completed. The host also monitors the socket connections for activity. After a predetermined period of inactivity on a client connection, the host automatically closes the connection to free up sockets, which may be a limited resource.

An example of the type of host processor which may be used in an ultrasound imager such as the LOGIQ 700 sold by General Electric Co., Milwaukee, Wis., is an MVME167 single board computer sold by Motorola Inc., of Sunnyvale, Calif., based on a Motorola™ 680x0 series central processor unit, or CPU. This host CPU is controlled by a real-time operating system such as pSOS™, available from Integrated Systems Inc., or VxWorks™, available from Wind River Systems Inc. The host functions described herein may exist as tasks, as defined in the context of such operating systems, or they may be functions or procedures called by other tasks.

Each command (or packet) sent to the host from a client is acknowledged with a special acknowledgement packet which contains an error code as well as any data requested by the client. Command and acknowledgement packets are fixed to a predetermined size, so that if a client needs to send extensive data to the host or vice versa, multiple packets may be required. The communications command structure is set up to support multiple packets using timestamps and sequence numbers to keep track of the packets.

The client computers (e.g., PCs or workstations) can run any of the task interface programs as remote processes. A task interface program includes a library of communication handlers and a task interface for the specific task function being run as a remote process. Client communication tasks include requesting a connection to the host, sending commands to the host, receiving a response from the host, and closing the connection. The communications library can support both asynchronous and blocking communications. In asynchronous communications, a command is sent to the host and control is returned immediately to the client without waiting for a response. When a response is received, a handler function is called to inform the client. In blocking communications, when a command is sent, the client waits (blocks) until a response is received. The choice of which type of communication to use depends on the particular client requirements.

Each command supported by the host is also supported in the client communications library. Associated with each command may be data structures describing the data to be sent and received. One library function, the command dispatcher, is used to send all commands, with the arguments of the function being a command ID number or type, the data to be sent, if any, a buffer where data to be received, if any, should be placed, and an optional "pointer to a handler" function to be called when the command is completed. Lower level functions which packetize and send the commands to the host are called by the command dispatcher function. If there are limited sockets available on the host, then a "well-behaved" client will close a connection as soon as the necessary command has been completed.

A task function interface can be as simple as command line arguments to a task program, or more sophisticated graphical user interfaces (GUIs), such as an X-Windows™ or OpenLook™ interface established on a Sun Microsystems workstation or Windows™ interface on a PC. Such GUIs may be built using standard software builder tools, such as Sun Microsystem's GUIDE™ builder for Sun workstations, or similar type of program for building Windows™—based GUIs to run on a PC, in order to create software buttons, slides, switches, and other hardware-emulated controls for the task function interfaces.

The communications system and method described above allows task functions for controlling the associated equipment to be distributed as remote processes run on other computers. For complex computerized equipment, such task functions can be computational and resource-intensive and can greatly burden the host processor's capabilities. The off-loading of resource-intensive task functions in the invention allows the task loadings for the associated equipment to be distributed and keeps the host processor from becoming overburdened. While remote processes have been used for some types of medical facilities, for example, in remote diagnostics or data acquisition or analyses at doctors' offices, they have not been previously known to be used for off-loading of task functions for controlling the equipment used during actual patient scanning.

Task Interfaces for Ultrasound Imager System

Task interfaces illustrative of the utility of the present invention are described below with respect to two types of task functions specific to an ultrasound imager system, i.e., shaping a waveform for transmission, and shading received signals for image resolution. These task interfaces also demonstrate certain improvements to the performance of these task functions in the ultrasound imager system.

Figure 2:
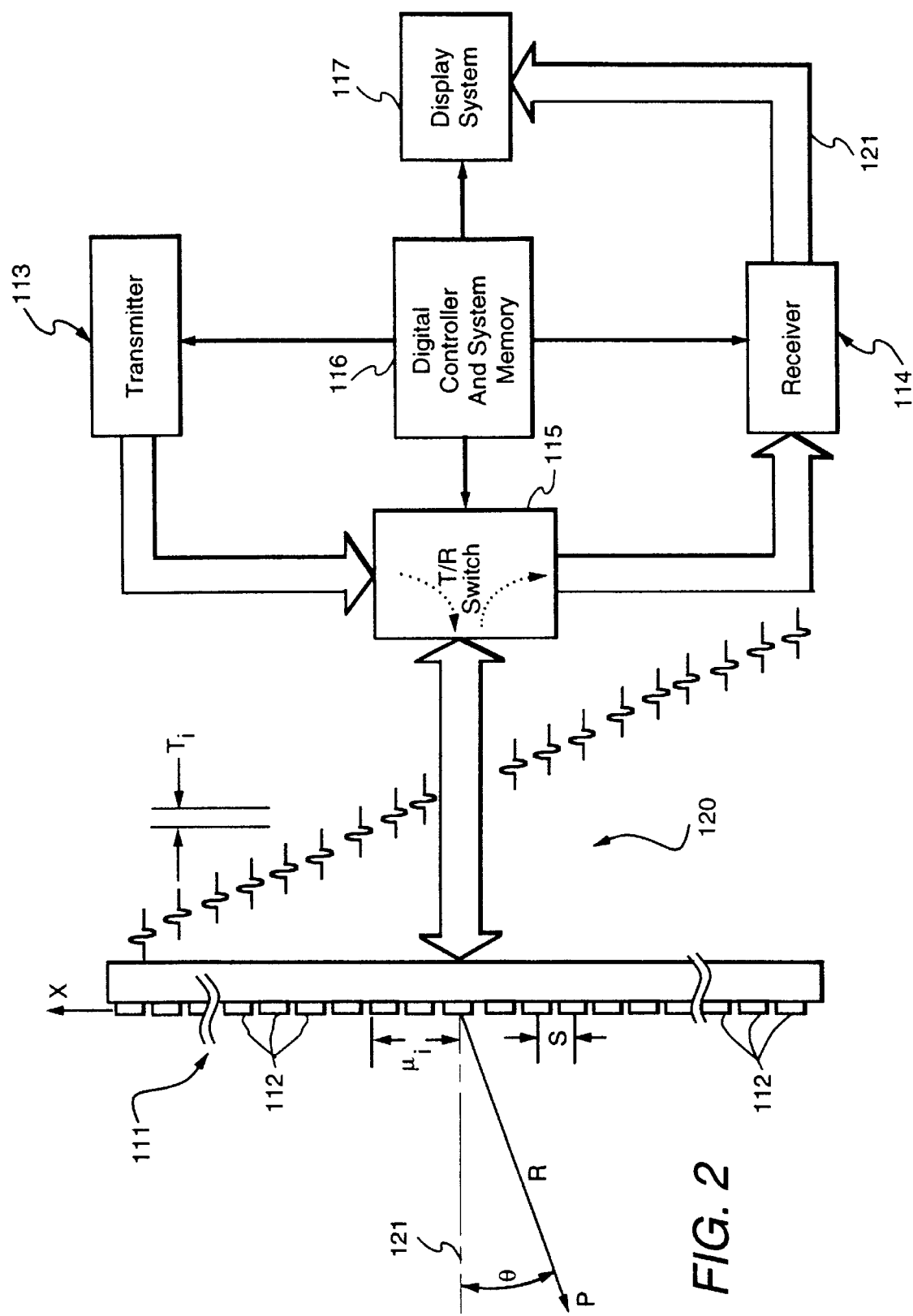
FIG. 2 is a block diagram illustrating overall operation of an ultrasound imager system.

Reference is made to FIG. 2 for an explanation of the basic operation of an ultrasound imager system. The system includes a transducer probe 1 11 having an array of piezoelectric elements 112 each of which produces a burst of ultrasonic energy when energized by pulsed waveform signals 120 produced by a transmitter 113. Coherent, steered beams of ultrasound energy R are produced by carefully controlling the timing of the firing of the transducer elements 112 so that the energy constructively interferes as directed waves scanned over a given area of the subject. The ultrasound beams penetrate the body of a subject under study, and echoes from underlying body structures, e.g., an object P, are reflected back to the transducer elements 112.

Timed switching of a set of transmit/receive (TIR) switches 115 allows transducer elements 112 to generate ultrasound energy from electrical signals, and to produce electrical signals upon receiving ultrasound energy. Analog echoes received by transducer elements 112 are converted to digital signals and sent to a receiver 114. The receiver 114 applies digital techniques for discriminating the echo signals and creating image signals of the reflecting structures in the body. Image resolution depends upon the transmitted waveform shape (which in turn depends on the pulse sequence and spacings S of the transducer elements), time delays Ti between transmitted waves or received echoes on adjacent transducer elements. Receiver 114 produces image signals 121 for display on a display system 117. Transmitter 113, receiver 114, T/R switches 115, and display 117 are operated under control of a digital controller and system memory 116.

An example of an ultrasound imager system is sold under the trademark LOGIQ 700 by General Electric Co., of Milwaukee, Wis. The imager has the capability of being used with a multi-row transducer 5, as shown schematically in FIG. 3a. The number of transducer elements in each row is optimized to provide improved out-of-plane (elevational) as well as normal in-plane (azimuthal) focusing. The rows are symmetrical and electrically wired together, element-wise, through conductors 17. The multiple rows improve the out-of-plane (elevational) focusing so as to reduce the overall voxel size. Reducing the voxel size improves resolution, for example, by producing more contrast for small, low-intensity features such as blood vessels.

Waveform Shaping Task Interface

Much effort goes into designing an optimum transmit waveform, since this affects image resolution and the amount of energy delivered into the body (which is regulated according to Food and Drug Administration guidelines). During integration of a new probe design or configuration of the ultrasound imager, the system engineer experiments with the transmit pulse signals generating the waveform until the transmit performance of the probe is optimized. This often requires trial and error and can be quite time consuming since each pulse signal waveform must be programmed into the system and tested. Due to complexity of the waveform, particularly for probes having multiple rows of piezoelectric elements, it would be very difficult to provide conventional types of hardware buttons, switches, and sliders to manually regulate the pulse amplitudes profile provided to the transducer elements.

In the present invention, the task function of shaping a waveform for transmission is off-loaded, as a remote process, from the host processor to a client processor. The task function is performed using a task interface which has been constructed with a graphical interface builder such as the previously mentioned GUIDE™ builder. The task interface provides software buttons, switches, and sliders which can be manipulated to specify the signal parameters for the waveform to be generated by the elements. The waveform parameters specified by a user on the remote process are then communicated to the host processor, using appropriate communication handlers, via the network connection. Multiple test versions of a waveform may be designed and stored remotely, and sent to the host for testing.

In the LOGIQ 700 imager, the transmit waveform is programmed by loading bit sequences into memory locations for each of the beamformer channels. Each bit represents a small fraction of the pulse sequence, and determines whether the pulser is on (bit=1) or off (bit=0) for the incremental period represented by the bit. The transmit waveform is constituted by the bit sequences stored for the beamformer channels, along with other parameters used for beamforming (there are multiple memory blocks for each channel). The transmit waveforms and constituents of the beamformer channels differ for different waveform shapes and different imaging modes.

Figure 4:
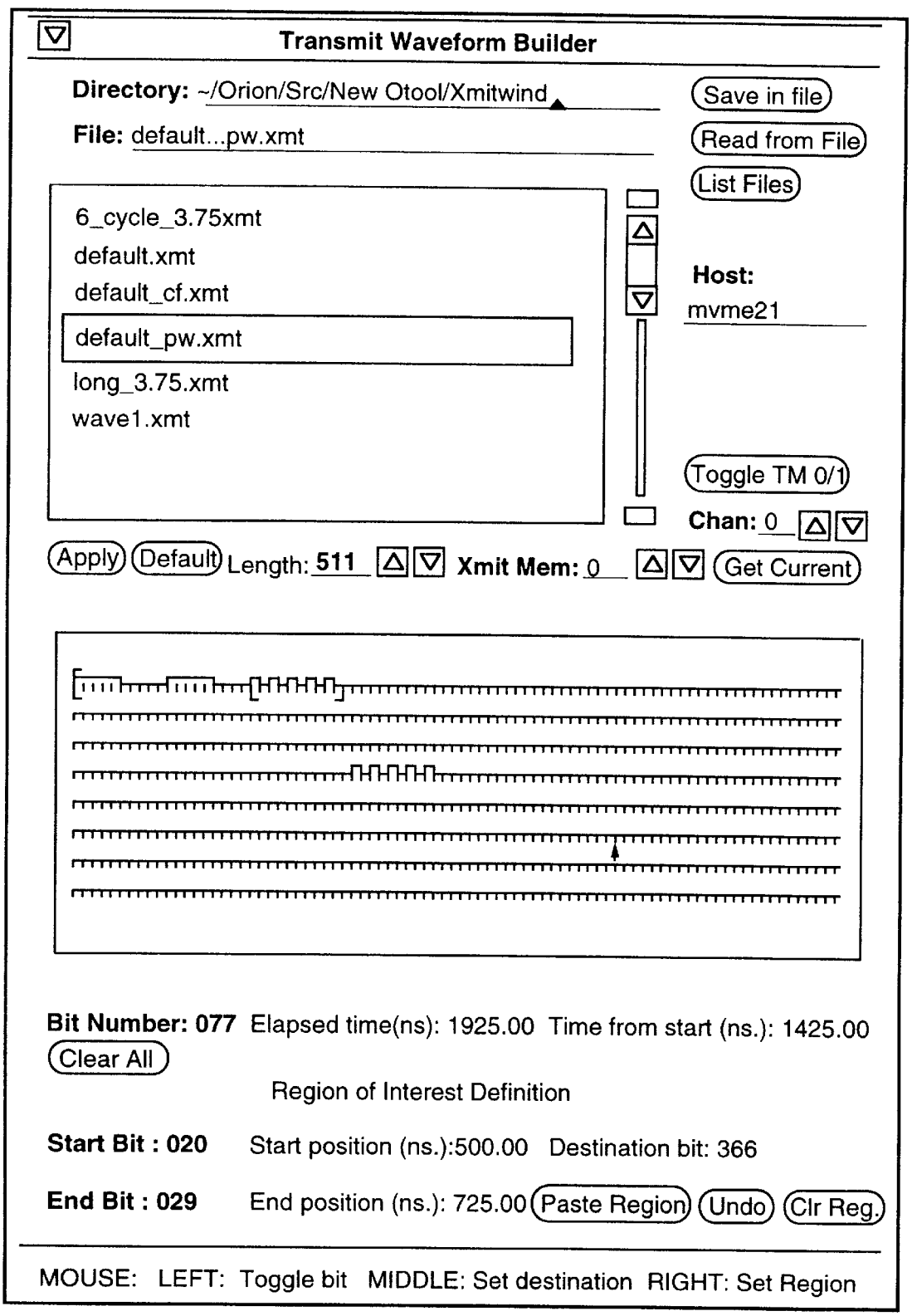
FIG. 4 is a view of a waveform shaping task interface for an ultrasound imager.

FIG. 4 is an example of a task interface used in the present invention for a Transmit Waveform Builder for the LOGIQ 700 system constructed using the GUIDE™ builder. The interface has a window divided into 3 parts, with the main part being the segmented graph in the middle of the window. The segmented graph contains the bit segments arranged across 8 lines, with tic marks defining each segment. Each segment represents one bit of a bit sequence to be stored in a memory block for a beamformer channel. The start of the bit sequence is denoted by the open bracket "[" at the left end of the first line. The user can set or clear a bit by moving a mouse pointer to the "cell" representing a bit, and then clicking on a mouse button to toggle the bit between 0 (cleared) and 1 (set). As the user moves the mouse over the graph area and sets or clears the segments of the bit sequence, the interface program updates the timing and position information displayed in the lower part of the window.

The user may define a "region of interest" which can be copied and pasted to another region of the graph. In the example shown in FIG. 4, the region of interest starts at bit number 20 (denoted by the bottom half of a left bracket "[", and ends at bit number 29 (denoted by the bottom half of a right bracket "]". The destination of the potential paste operation is the bit indicated by the small arrow pointing towards the waveform axis. A paste operation copies the waveform portion delimited by start and end brackets to the bit location designated by the pointer by clicking on the "Paste Region" button with the mouse. The "Undo" button is used for performing an undo operation by mouse click. All bits in the region of interest may be cleared by clicking on the "Clr Reg" button on the lower portion of the window. The "Clear All" button is used to set all bits in the waveform to 0.

The upper part of the task interface has functions and fields for saving and retrieving waveforms stored in files, listing files, and communicating with the host for the imager. After constructing a bit-sequence for a desired waveform, the user may download it to the host for the LOGIQ 700 imager via the previously described communication procedures by clicking on the "Apply" button. Since there are several memory blocks per channel, the "Xmit Mem" field is used to select the block the bit sequence is to be downloaded to or later retrieved from. The "Chan" field is used for waveform retrieval from the host to designate the number of the designated beamformer channel from which the waveform will be retrieved. The "Host" field contains the network name for the target host system.

The user may also save the waveform in a file on the client system by entering the "Directory" and "File" names in the corresponding fields at the top part of the window, then clicking on the "Save in File" button. Similarly, an existing file can be read into the window using the "Read from File" button. If the "List Files" button is clicked, the interface program searches the designated Directory of the client workstation for waveform files, such as all files ending with the suffix ".xmt", and displays any names found in the scrollable list. The user may also request the current waveform used by the target imager by clicking on the "Get Current" button. Any waveform retrieved from the imager can be edited and downloaded to the imager or saved in a file if desired.

Shading Task Interface for Ultrasound Imager System

A shading task interface provides an intuitive and graphical tool for a user to observe and modify the parameters for controlling the different kinds of apertures that may be used by the transducer for receiving and converting echo signals from a subject into image signals. Having a client run a remote process for setting the shading values through a programmed interface reduces the loading on the imager and avoids the use of dedicated buttons and sliders and any need for crowding the operator console of the imager.

In the example of the GE LOGIQ 700 imager, a facility is provided for constructing a dynamically expanding and/or asymmetrically shaded aperture for reception by the transducer elements. Since the multi-row probe has more electrically independent elements than available beamformer channels, a multiplexing scheme is used to receive the echo signals. As an example, a synthetic aperture (SAFT) scheme may be used where each direction of a scan is fired and received twice, with the aperture being switched to different portions of the transducer between successive firings. The two firings occur in rapid succession so that data from the two receive beams can be added coherently. FIGS. 3b and 3c show the SAFT aperture multiplexing scheme in which a subset of elements comprising a shaded "inner aperture" 18 (shown cross-hatched) is activated for receiving a first firing (FIG. 3b), and a shaded "outer aperture" 19 (shown cross-hatched) is activated for receiving a second firing (FIG. 3c).

With only five rows in the multi-row probe, the elevational direction is very coarsely sampled; hence focusing in the elevational direction is poorer than in the azimuthal direction. Both static and dynamic aperture shading must be applied to optimize the elevational performance of these probes. Static shading is used to set an overall apodization (shading) value per row of the multi-row transducer. This shading does not vary dynamically as the ultrasound receive beam is continuously focused during the receive mode. However, because of the two different subapertures in multiplexing, different transducer elements will be connected to different beamformer channels during alternate SAFT firings. Control of the static shading values must take this multiplexing of beamformer channels to transducer rows into account.

Following initiation of a master timing signal for each imaging cycle, a predetermined transmit interval begins with the transducer elements launching an acoustic impulse produced by pulser circuitry in accordance with the bit sequences retrieved for the beamformer channels. After the transmit interval, the receive interval is counted so that echo signals from progressively deeper levels in the subject body are captured. The interval between successive firings is chosen to allow capture of echoes from the deepest level as needed. Dynamic shading values are used to attenuate the echo signals received according to a profile which has the effect of forming a dynamically expanding aperture for signal capture at progressively deeper levels.

Figure 5:
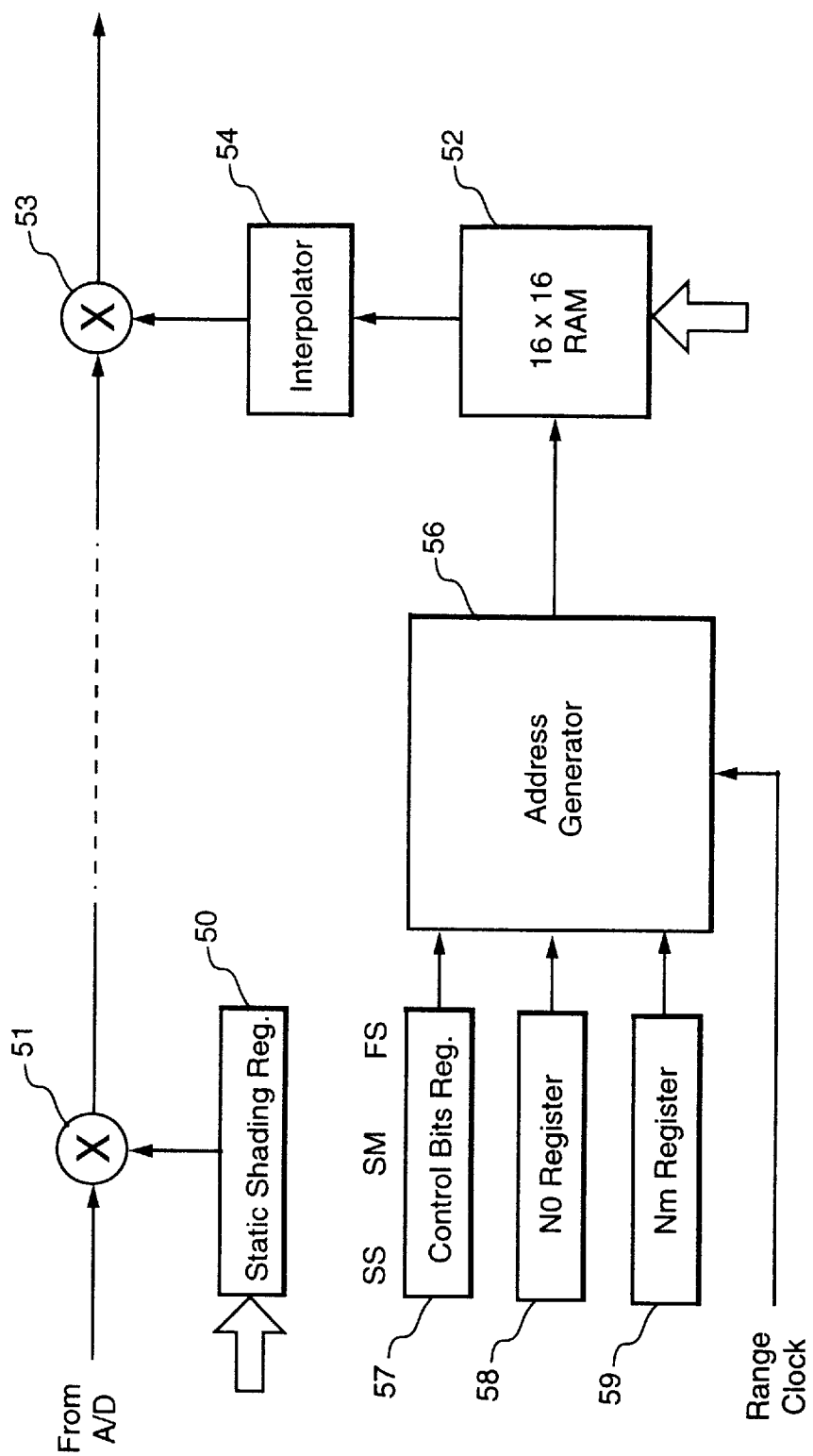
FIG. 5 is a block diagram of shading circuitry for an ultrasound imager.

FIG. 5 illustrates a highly simplified view of shading circuitry which can be implemented on a receiver chip of the imager system. Each channel of the transducer is connected to an A/D (analog-to-digital) converter. Data coming from the converter is scaled by multiplying it in a static shading multiplier 51 by a static shading value stored in a static shading register 50. After a substantial amount of further processing, including demodulation and filtering (not shown), the data is scaled again by multiplying it in a dynamic shading multiplier 53 by a dynamic shading value taken from a random access memory (RAM) 52. To conserve memory space, the RAM 52 has space for only a small number of values, and an interpolator 54 is used for creating additional values between the stored values. To generate unique dynamic shading values for each channel of the transducer, an address generator 56 is used to address the shading values stored in RAM 52 in synchronization with reception of the transducer data in accordance with clock intervals counted by a range clock. Control bits register 57, N0 register 58, Nm register 59, and a range clock provide inputs for controlling or altering the mode of operation of address generator 56.

The static shading values for register 50 and the dynamic shading values for RAM memory 52 of the shading circuitry are provided from the host controller to the imager based on values downloaded or saved from a shading task function run by a client in communication with the host. Ideally, separate and independent dynamic shading profiles are used for each channel of a multi-row probe. However, due to trade-offs made with available on-chip memory, it may not be feasible to have a separate dynamic shading profile for each channel. A compromise is implemented in the LOGIQ 700 imager system by loading a single dynamic shading profile applicable to all channels, then using a different static shading value for the channels of each row of the transducer to scale the dynamic shading profile for each row.

Figure 6:
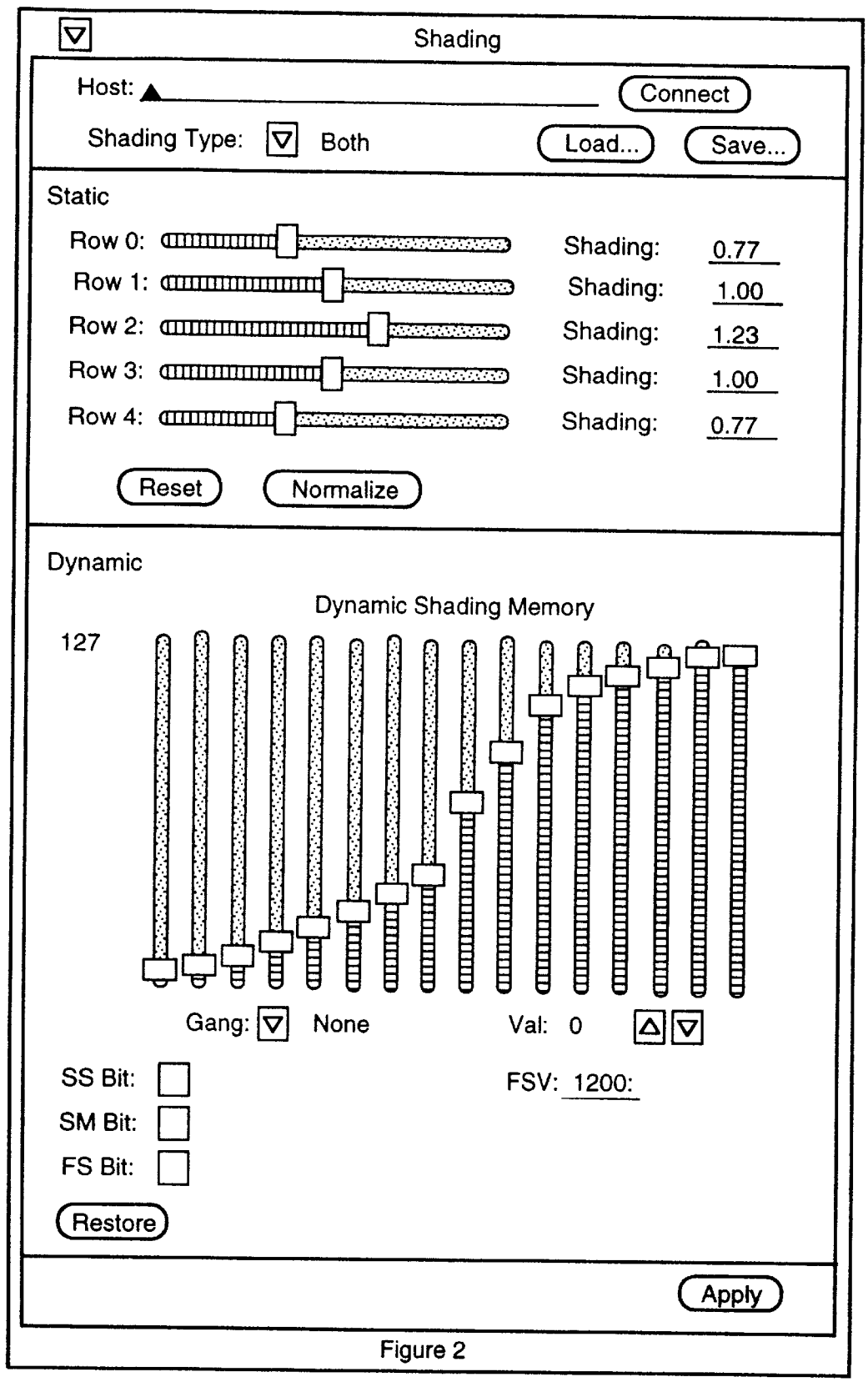
FIG. 6 is a view of a shading task interface for the ultrasound imager.

FIG. 6 is an example of a Shading task interface for a client, used to configure the static shading values on a per-row basis and dynamic shading values with a single profile. A Host and File Management subwindow allows the user to establish a network connection between the shading task and the host by clicking the "Connect" button, reading a file containing the transducer shading values by clicking on "Load", and saving the modified shading values to a file by clicking on "Save". A Static Shading subwindow allows the user to set the shading values for each of the 5 rows of the transducer. The user can modify the static shading values by clicking on the slide buttons of the graphical interface. Similarly, a Dynamic Shading subwindow allows the user to view and modify the range-dependent shading profile which is common to all channels. A set of 16 graphical sliders is provided to set the 16 values to be stored in the shading circuitry RAM. Check boxes are also provided for setting the SS, SM, and FS bits of the control bits register 57 (shown in FIG. 5 and described further below). The "Apply" button allows the user inputs (values of the sliders and check boxes) to be downloaded to the imager system.

Figure 7:
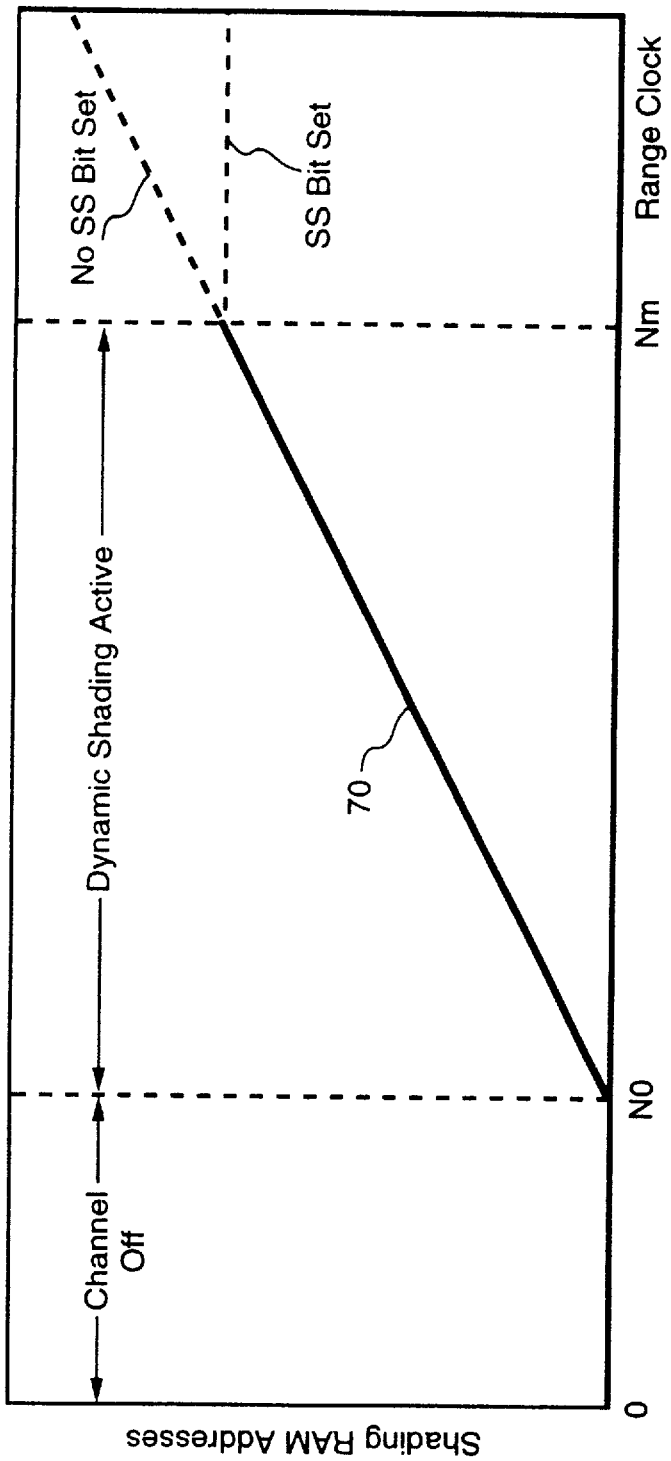
FIG. 7 is a graphical diagram of an alternative dynamic shading mode for the ultrasound imager.

As an alternative, a simpler shading mode may be used for generating the aperture shading of the transducer elements. This alternative mode is illustrated in FIG. 7. When the SM bit in the control bits register of the shading circuitry is set, address generator 56 (FIG. 5) is operated to generate a linear ramp 70 of RAM addresses based upon the number of range clock ticks that have elapsed since the NO register has counted down to zero, indicating that the channel should begin contributing data. If the SS (shading stop) bit of control bits register 57 (FIG. 5) is not set, the ramp continues incrementing as long as the range clock is counting. If the SS bit is set, the ramp stops incrementing and holds its last value after an Nm register has counted down, indicating that the window for receiving data from the channel is closed.

Thus the invention allows the resource-intensive task functions for controlling complex equipment, such as the above-described ultrasound imager system, to be off-loaded to client processors as remote processes from the host processor. Graphical user interfaces for the task functions provide software buttons, switches, and sliders for setting the system parameters, and communication handlers send these parameters to the host processor. This software approach to distributed system control reduces the need to add hardware buttons, switches, etc. to the system and may reduce computational loadings at the host. Instead of one large monolithic controller, each task function may be operated and maintained separately. Multiple instances of the task functions may be run remotely without tying up the host.

Other Improvements

Existing complex equipment, such as ultrasound imagers, have a keyboard interface which the operator uses to input parameters of the machine during an ultrasound examination. To change parameters during the examination, the operator must use one hand to interact with the keyboard, while holding the probe in the desired position on the patient's body with the other hand. This can be awkward for the operator. In addition, the position of the keyboard has to be changed depending on whether the operator is left or right handed.

Figure 8:
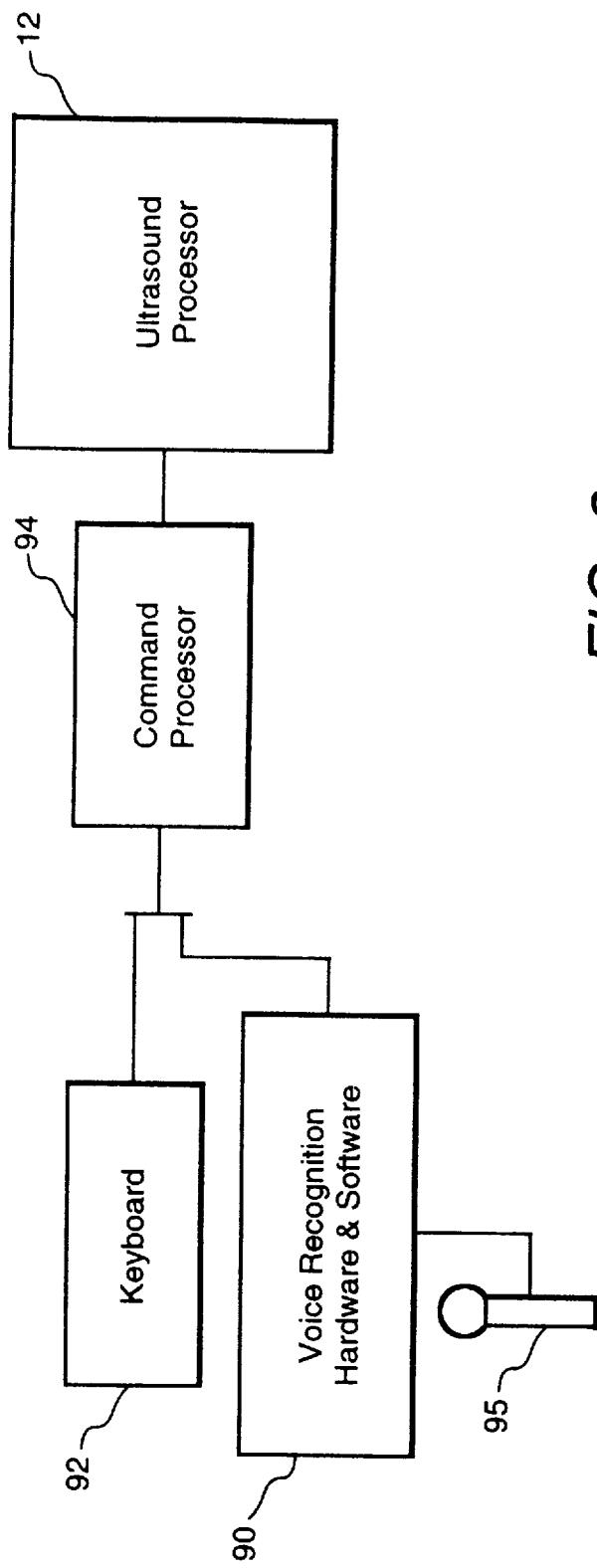
FIG. 8 is a block diagram of a system for implementing voice input to an ultrasound imager system via input hardware and software.

An improved operator interface provides for voice command input to the machine to bypass or minimize the need to use the keyboard during scanning. Voice recognition systems are currently available which allow a system to be trained to recognize the vocabulary and voice characteristics of an operator, and even to allow single words to invoke a sequence of commands. FIG. 8 shows one voice input configuration in which a voice recognition system 90 (including a microphone 95) is coupled in parallel with a keyboard 92 to a front-end command processor 94 for host processor 12 of the ultrasound imager system. This approach requires minimal modification to the imager system, but requires integration of the voice recognition system with the command processor and imager operating system.

Figure 9:
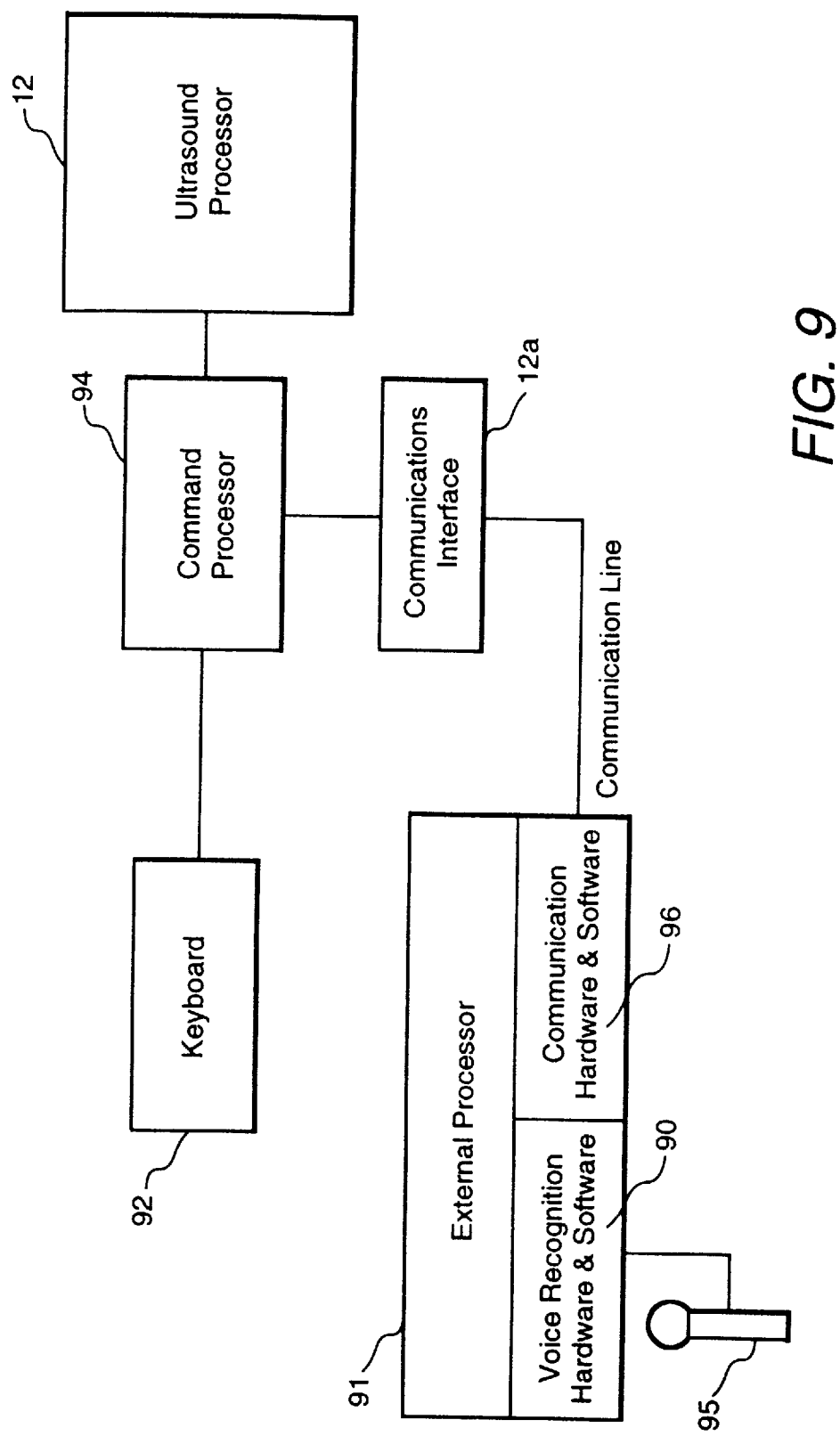
FIG. 9 is a block diagram of a system for implementing voice input to the imager system as a remote process.

FIG. 9 illustrates another voice input configuration having the voice recognition system 90 (and microphone 95) interfaced with its own external processor 91 at a remote location, and which is coupled through a communication line (including hardware and software 96) to the communications task interface 12a for ultrasound processor 12 (see FIG. 1). In this approach, the ultrasound host accepts normal keyboard inputs and, in addition, listens on its communication sockets for requests from voice recognition processor 91 running voice input as a remote process. The off-loading of voice recognition reduces the load on the imager host and allows easier maintenance and upgrades.

While only certain preferred features of the invention have been illustrated and described, many modifications and changes will occur to those skilled in the art. It is, therefore, to be understood that the appended claims are intended to cover all such modifications and changes as fall within the true spirit of the invention.

We claim:

1. A system for controlling complex equipment which is operated by a plurality of computerized task functions, comprising:

(a) a host processor coupled to the complex equipment for controlling operation of the plurality of task functions;

(b) a plurality of client processors each having processing means for running a selected task function of the complex equipment as a remote process therefrom;

(c) a communications network coupling the host processor to the client processors, said host and client processors being provided with respective communication handlers operable with said network for requesting connection of any of the client processors to the host processor, sending commands from the client processor to the host processor, handling of commands by the host processor, communicating responses to commands from the host processor to the client processor, and closing the connection with the host processor; and (d) a plurality of task interface programs each providing a respective task interface for running a selected task function of the complex equipment on any of the client processors, wherein a task interface program corresponding to the selected task function requested by a client processor resides on the client processor so that the task function can be run as a remote process on the client processor through the corresponding task interface.

2. The system as defined in claim 1, wherein said respective task interface comprises communications task means for listening for connection requests from any of said client processors on a plurality of communications channels of said network and for establishing connections with the client processors and handling commands sent therefrom in a prioritized order.

3. The system as defined in claim 2, wherein said respective task interface comprises background task means for performing the commands sent from said client processors which are prioritized in order by said communications task means as a background function.

4. The system as defined in claim 3, wherein said communications task means is adapted to prioritize the commands from said client processors in a queue to be performed by said background task means.

5. The system as defined in claim 1, wherein the complex equipment comprises an ultrasound imager system provided with a probe having an array of transducer elements for transmitting an ultrasound wave in response to transmit waveform signals applied to the transducer elements and for converting echoes received by the transducer elements into ultrasound image signals for display by said imager system.

6. The system as defined in claim 5, wherein said ultrasound imager system is adapted to perform task functions including shaping a transmit waveform by specifying its transmit waveform signals, and shading received echoes by specifying attenutation parameters applied to the transducer elements.

7. The system as defined in claim 6, wherein said plurality of task interface programs includes a waveform shaping task interface program for allowing a client processor to run a waveform shaping task interface as a remote process for specifying transmit waveform signals for shaping a transmit waveform.

8. The system as defined in claim 6, wherein said plurality of task interface programs includes a shading task interface program for allowing a client processor to run a shading task interface as a remote process for specifying attenutation parameters for shading reception of echoes through the transducer elements.

9. The system as defined in claim 5, including a voice recognition system and an external processor, said voice recognition system being interfaced with said external processor, said external processor being coupled to said host processor through said communications network for operating a voice input task function for the ultrasound imager system as a remote process on the external processor.

10. A system as defined in claim 5 including a voice recognition system is coupled to said host processor through said communications network for operating a voice input function for the ultrasound imager system.

11. A method for controlling complex equipment which is operated by a plurality of task functions, comprising:

(a) providing a host processor coupled to the complex equipment for controlling operation of the plurality of task functions;

(b) providing a plurality of client processors each having processing means for running a selected task function of the complex equipment as a remote process therefrom;

(c) coupling the host processor to the client processors via a communications network, said host and client processors being provided with respective communication handlers operable with said network for requesting connection of any of the client processors to the host processor, sending commands from the client processor to the host processor, handling of commands by the host processor, communicating responses to commands from the host processor to the client processor, and closing the connection with the host processor; and (d) constructing a plurality of task interface programs each providing a respective task interface for running a selected task function of the complex equipment on any of the client processors.

12. The method as defined in claim 11 wherein, said task interface comprises communications task means for listening for connection requests from any of said client processors on a plurality of communications channels of said network and for establishing connections with the client processors and handling commands sent therefrom in a prioritized order.

13. The method as defined in claim 12 wherein said task interface comprises background task means for performing the commands from said client processors which are prioritized in order by said communications task means as a background function.

14. The method as defined in claim 11, wherein said communications task means is adapted to prioritize the commands from said client processors in a queue to be performed by said background task means.

15. The method as defined in claim 11, wherein the complex equipment comprises an ultrasound imager system provided with a probe having an array of transducer elements for transmitting an ultrasound wave in response to transmit waveform signals applied to the transducer elements and for converting echoes received by the transducer elements into ultrasound image signals for display by said imager system.

16. The method as defined in claim 15, wherein the ultrasound imager system is adapted to perform task functions including shaping a transmit waveform by specifying its transmit waveform signals, and shading received echoes by specifying attenutation parameters applied to the transducer elements.

17. The method as defined in claim 16, wherein the plurality of task interface programs includes a waveform shaping task interface program for allowing a client processor to run a waveform shaping task interface as a remote process for specifying transmit waveform signals for shaping a transmit waveform.

18. The method as defined in claim 16, wherein said plurality of task interface programs includes a shading task interface program for allowing a client processor to run a shading task interface as a remote process for specifying apodization parameters for shading reception of echoes through the transducer elements.

19. The method as defined in claim 15, further comprising the step of providing a voice recognition system interfaced with an external processor coupled to said host processor through said communications network for operating a voice input task function for the ultrasound imager system as a remote process on the external processor.

20. The method as defined in claim 15, further comprising the step of providing a voice recognition system coupled to said host processor through said communications network for operating a voice input function for the ultrasound imager system.

* * * * *